United States Patent [19]

Inoue et al.

[11] 4,198,304
[45] Apr. 15, 1980

[54] COMPOSITIONS CONTAINING BETA SUBSTITUTED ACRYLIC ACID AMIDES AS PRESERVATIVES

[75] Inventors: Shigeo Inoue, Miyashiromachi; Norioki Miyamoto, Sakura; Haruo Shimizu, Funabashi, all of Japan

[73] Assignee: Kao Soap Co., Ltd., Tokyo, Japan

[21] Appl. No.: 719,731

[22] Filed: Sep. 2, 1976

[30] Foreign Application Priority Data

Sep. 11, 1975 [JP] Japan .................................. 50/110374

[51] Int. Cl.$^2$ ..................... A61K 31/10; A61K 31/16; A61L 13/00; C11D 3/48; C10M 3/32
[52] U.S. Cl. ..................................... 252/47.5; 252/11; 252/106; 252/173; 252/355; 252/526; 252/545; 260/561 N; 260/561 S; 424/320; 424/337; 260/112 R; 260/398.5; 536/1
[58] Field of Search ............... 424/320, 699, 324, 337; 260/561 N, 561 S, 112 R, 398.5; 252/106, 526, 545, 11, DIG. 5, DIG. 4, 355, 1, DIG. 14, 173, 47.5; 531/1

[56] References Cited

U.S. PATENT DOCUMENTS

| | | | |
|---|---|---|---|
| 2,899,354 | 8/1959 | Kleemann | 260/461 S |
| 3,437,685 | 4/1969 | Brust | 260/481 |
| 3,541,119 | 11/1970 | Richter | 260/397.6 |
| 3,663,623 | 5/1972 | Crovetti | 260/607 A |
| 3,821,399 | 6/1974 | Richter | 424/304 |
| 3,914,301 | 10/1975 | Miller | 260/561 S |
| 4,021,482 | 5/1977 | Schempp | 260/561 S |

*Primary Examiner*—Dennis L. Albrecht
*Attorney, Agent, or Firm*—Blanchard, Flynn, Thiel, Boutell & Tanis

[57] ABSTRACT

Compounds having the formula:

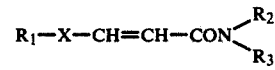

wherein $R_1$ is alkyl or alkenyl containing 1 to 20 carbon atoms, X is S, SO or $SO_2$, and $R_2$ and $R_3$, which can be the same or different, are hydrogen, alkyl containing 1 to 20 carbon atoms, oxyalkylene containing 1 to 20 units of ethylene oxide or propylene oxide, 2-sulfoethyl or a salt thereof, or 2-carboxyethyl or a salt thereof, are incorporated, as a preservative or anti-microbial agent in compositions that are subject to deterioration by the action of micro-organisms, excluding foods and medicines.

12 Claims, No Drawings

COMPOSITIONS CONTAINING BETA SUBSTITUTED ACRYLIC ACID AMIDES AS PRESERVATIVES

CROSS-REFERENCE TO RELATED APPLICATIONS

This application is related to U.S. Ser. No. 699,324, filed June 24, 1976, now abandoned and replaced by Ser. No. 807,509, and U.S. Ser. No. 702,405, filed July 6, 1976, now abandoned and replaced by Ser. No. 818,951, the entire contents of which are incorporated herein by reference.

The present invention relates to non-pharmaceutical compositions which are subject to deterioration by the action of micro-organisms and which contain as a preservative, one or a mixture of compounds having the formula (I):

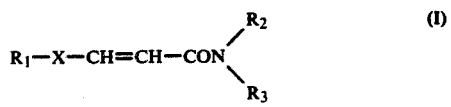

wherein $R_1$ is alkyl or alkenyl containing 1 to 20 carbon atoms, X is S, SO or $SO_2$, and $R_2$ and $R_3$, which can be the same or different, are hydrogen, alkyl containing 1 to 20 carbon atoms, oxyalkylene containing 1 to 20 units of ethylene oxide or propylene oxide, 2-sulfoethyl or a salt thereof, or 2-carboxyethyl or a salt thereof.

The present inventors have often utilized different conventional antimicrobial agents as germicides, fungicides or antiseptics, but various problems have been encountered in their use. The different conventional antimicrobial agents were developed for the initial purpose of obtaining antimicrobial activity, but those that were supposed to have an extensive scope of usefulness at the time of their initial development often proved to be unsatisfactory as applied to new systems or compositions.

In order to overcome the microbial deterioration of cosmetics and housekeeping sundries, for example, it is conventional to measure first the degree of antimicrobial activity independently from the physico-chemical features of the system, for example, by admixing antimicrobial agents such as benzoic acid, and aromatic phenol compounds for example salicylic acid or alkali salts thereof, p-hydroxybenzoic acid esters, p-isopropyl-o-methylphenol or o-phenylphenol, or by adding the so-called invert soaps such as alkylbenzyldimethylammonium halides, and then examine their compatibility and stability in the mentioned systems for a long time period. However, these examinations require long-term testing of numerous chemicals for many test items. It is generally found that very few chemicals are satisfactory for a particular purpose. Furthermore, different systems of chemicals require the same test processes so that many tests must be carried out repeatedly and many man-hours are required to do the testing. This presents serious difficulties to the plan of developing the market for these compositions. In addition, because the conventional antimicrobial chemicals mentioned above have been utilized for a long period and in wide ranges of amounts, many resistant microorganisms have appeared and prevention of microbial contamination, for example, in production plants, is very difficult.

Therefore, it is desired to provide more chemicals having an excellent and wide-ranging antimicrobial activity for use in various compositions.

We have found that the formula (I) compounds have both physicochemical properties and antimicrobial activity that make them highly effective for use as preservatives in various compositions, such as cosmetics.

The formula (I) compounds include the following typical examples:

1. β-alkylsulfenyl-acrylic acid amides, for example, $n-C_8H_{17}-S-CH=CH-CONH_2$ ($n_D^{20}=1.5168$)
2. β-alkylsulfinyl-acrylic acid amides, for example,

3. β-alkylsulfonyl-acrylic acid amides, for example,

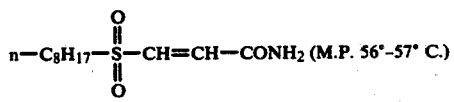

4. β-alkylsulfenylacrylic acid dialkylamides, for example,

5. β-alkylsulfinyl-acrylic acid dialkylamides, for example,

6. β-alkylsulfonyl-acrylic acid dialkylamides, for example,

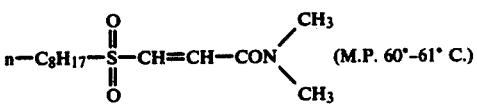

7. β-alkylsulfenyl-acrylic acid di-(2-hydroxyethyl)-amides, for example, $n-C_8H_{17}-S-CH=CH-CON(CH_2CH_2OH)_2$ ($n_D^{20}=1.5272$)
8. β-alkylsulfinyl-acrylic acid di(2-hydroxyethyl)-amides, for example,

9. β-alkylsulfonyl-acrylic acid di-(2-hydroxyethyl)-amides, for example,

10. β-alkylsulfenyl-acrylic acid 2-sulfoethylamides, for example, n—C$_8$H$_{17}$—S—CH=CH—CONHCH$_2$CH$_2$SO$_3$Na (M.P. 86°–87° C.)

11. β-alkylsulfinyl acrylic acid 2-sulfoethyl amides, for example,

n-C$_8$H$_{17}$S—CH=CH—CONHCH$_2$CH$_2$SO$_2$Na (M.P. 54°–55° C.)

12. β-alkylsulfonyl-acrylic acid 2-sulfoethylamides, for example,

n-C$_8$H$_{17}$—S—CH=CH—CONHCH$_2$CH$_2$SO$_3$Na (M.P. 110°–112° C.)

13. β-alkylsulfenyl-acrylic acid 2-carboxyethylamides, for example, n—C$_8$H$_{17}$—S—CH=CH—CONHCH$_2$CH$_2$COONa (M.P. 57°–58° C.)

14. β-alkylsulfinyl-acrylic acid 2-carboxyethylamides, for example,

n-C$_8$H$_{17}$—S—CH=CH—CONHCH$_2$CH$_2$COONa (M.P. 49°–50° C.)

15. β-alkylsulfonyl-acrylic acid 2-carboxyethylamides, for example,

n-C$_8$H$_{17}$—S—CH=CH—CONHCH$_2$CH$_2$COONa (M.P. 89°–90° C.)

The formula (I) compounds of the invention are prepared as follows:

A mercaptan having the formula:

R$_1$-SH     (II)

wherein R$_1$ has the same meaning as defined above, is reacted with acetylene-monocarboxylic acid, in an aqueous solution of an alkali metal hydroxide, to form β-sulfenylacrylic acid having the formula:

R$_1$—S—CH=CH—COOM     (III)

wherein M is hydrogen or alkali metal, and R$_1$ has the same meaning as defined above. Then the obtained β-sulfenylacrylic acid (III), or the β-sulfenylacrylic acid halide obtainable by halogenation of the formula (III) compound, is reacted with an amine having the formula:

$$\begin{matrix} R_2 \\ R_3 \end{matrix} \!\!\!\!> NH \quad (IV)$$

wherein R$_2$ and R$_3$ have the same meanings as defined above, to form the formula (I) compound wherein X is S. The last-mentioned compound is oxidized by an inorganic peroxide such as sodium meta-periodate or hydrogen peroxide, or by an organic peroxide such as m-chloroperbenzoic acid, perbenzoic acid or peracetic acid, to form the formula (I) compound wherein X is SO or SO$_2$.

The formula (I) compounds have properties which make them suitable for incorporation in cosmetic and detergent compositions such as creams, lotions, shampoos and rinses, and the formula (I) compounds exhibit antimicrobial preservative activity therein.

The aforementioned compounds 1, 2 and 3 cannot directly constitute the base or vehicle for pasty, creamy or liquid cosmetics and sundries, but in compositions containing other long-chain aliphatic compounds as the principal base or vehicle ingredients, the compounds 1, 2 and 3 have good compatibility due to their aliphaticity, and they exhibit bactericide, fungicide, and antiseptic activity. Similarly, the compounds 4, 5 and 6 are compatible with hydrocarbon compounds and have an excellent antimicrobial activity.

The compounds 7, 8 and 9 have physical properties similar to those of palm oil fatty acid diethanolamide or lauric acid diethanolamide, which are recommended as ingredients of high-quality liquid detergents, shampoos, rinses and cleansing cosmetics. Among them, compounds having alkyl groups containing 8 to 12 carbon atoms exhibit a foaming effect and a viscosity improving effect similar to those of lauric acid diethanolamide, as well as a detergent effect and a dispersing effect. Furthermore the adduct of 8 to 10 moles of ethylene oxide has a surfactant activity, like that of a non-ionic surfactant, and is excellent in wettability and dispersibility, thus being effective as a dispersion base for cosmetics and sundries.

The compounds 10, 11 and 12 have a cleaning power, dispersion power and wetting power as effective as those of sodium N-alkanoyl taurate and sodium N-methyl-N-alkanoyl taurate, which are anionic surfactants. Accordingly, they are most suitable as the base having antimicrobial activity for the anionic formulations such as shampoos and liquid detergents.

The compounds 13, 14 and 15 have properties similar to those of N-alkanoyl-β-alanine, a surfactant of the amphoteric type, and are suitable for use in shaving creams, for example, to enhance synergically the foamability and viscosity.

As described hereinbefore, because the formula (I) compounds have antimicrobial activity and various physico-chemical properties that make them effective for use as the base or an ingredient of a cosmetic or detergent base, they are usable as a base having microbial activity and they have excellent characteristics that have not been found in the conventional antimicrobial agents.

The mixing proportion of the formula (I) compound in the composition in which it is used varies widely depending on the purpose to be served and whether it is to be used for its antimicrobial preservative or antiseptic activity alone, or for its combined effect as a cosmetic or detergent base and as an antimicrobial agent.

In the first case wherein only antimicrobial activity of the compound according to the invention is desired, it is preferred to use 0.05 to 5 wt.% of the formula (I) compound wherein R$_1$ is alkyl or alkenyl containing 1 to 8 carbon atoms, preferably 2 to 8 carbon atoms, most preferably 4 to 8 carbon atoms.

On the other hand, when it is desired to obtain the dual activity as the base or a base ingredient for the composition and its antimicrobial effect, it is preferred to use 1 to 25 wt.% of the formula (I) compound wherein R$_1$ is alkyl or alkenyl containing 6 to 20 carbon atoms, preferably 6 to 18 carbon atoms, most preferably 8 to 16 carbon atoms. Thus, the quantity to be used of the compound according to the present invention varies depending on the properties of the composition in which it is used, its activity as the base component and its antimicrobial effect. The quantity may be selected according to these criteria.

According to this invention, the compound of the formula (I) may be incorporated into compositions as shown below.

A liquid detergent composition consists essentially of 10 to 50% by weight, preferably 15 to 30%, of one or more surfactants selected from anionic surfactants, nonionic surfactants and zwitter-ionic surfactants, 1 to 15% by weight, preferably 3 to 10%, of a stabilizer and the balance of water. As the anionic surfactants, there may be used alkali metal salts and alkanol amine salts, for example alkylbenzenesulfonate having alkyl group of 10 to 16 carbon atoms, alkanesulfonate having 10 to 20 carbon atoms, alkyl sulfate having 10 to 20 carbon atoms and polyoxyethylenealkylethersulfate having alkyl of 10 to 20 carbon atoms and 1 to 20 ethylene oxide units. As the nonionic surfactants, there may be used polyoxyethylenealkylether having alkyl of 10 to 20 carbon atoms and 5 to 20 ethyleneoxide units, polyoxyethylenealkylphenylether having alkyl of 8 to 12 carbon atoms and 5 to 20 ethylene oxide units and fatty acid alkylolamide derived from a fatty acid of 10 to 20 carbon atoms. As the zwitter-ionic surfactants, there may be used betain, sulfobetain, an imidazol-type surfactant having a long chain alkyl group of 10 to 20 carbon atoms. As the stabilizer, there may be used for example lower alcohols of 1 to 4 carbon atoms such as ethanol and propanol and glycols such as ethyleneglycol and propyleneglycol, urea and aromatic sulfonates such as toluene sulfonate and xylene sulfonate.

An oil-in-water emulsion cutting oil composition consists essentially of 85 to 95% by weight of liquid paraffin and 5 to 15% by weight of one or more organic surfactants selected from anionic surfactants and nonionic surfactants as defined above.

A cosmetic composition consists essentially of 10 to 70% by weight, preferably 15 to 50%, of oil or fat component selected from liquid paraffin and vegerable oil such as olive oil, castor oil, lanolin alcohol, lanolin ester and fatty acid ester, 3 to 40% by weight, preferably 10 to 30%, of one or more organic surfactants selected from anionic surfactants such as fatty acid salts (soap), alkylsulfate of 10 to 20 carbon atoms, and polyoxyethylenealkylethersulfate having alkyl of 10 to 20 carbon atoms and 1 to 10 ethylene oxide units and nonionic surfactants such as polyoxyethylenealkylether having alkyl of 10 to 20 carbon atoms and 1 to 10 ethyleneoxide units, fatty acid monoglyceride and sorbitol fatty acid ester, and 10 to 50% by weight, preferably 15 to 40%, of water.

A shampoo composition consists essentially of 5 to 35% by weight, preferably 8 to 20%, of anionic organic surfactants selected from alkyl metal salts and alkanolamine salts of alkylbenzene sulfonate having alkyl of 10 to 16 carbon atoms, those of alkyl sulfate having alkyl of 10 to 20 carbon atoms, those of alkanesulfonate of 10 to 20 carbon atoms, those of alpha-olefinesulfonate of 10 to 20 carbon atoms and those of polyoxyethylenealkylethersulfate having alkyl of 10 to 20 carbon atoms and 1 to 10 ethyleneoxide units, optionally containing nonionic surfactant, zwitter-ionic surfactant, oil and fat component, stabilizer and chelating agent.

The antimicrobial effect of the compound according to this invention is generally greater in order of —S—, —SO$_2$— and —SO— as X of the formula I, however the effect, particularly to mold fungi, is greater in order of —SO—, —SO$_2$— and —S—.

The present invention will be further described by reference to the following illustrative examples.

EXAMPLE 1

The effect of the sulfenyl, sulfinyl and sulfonyl groups of the formula (I) compounds on the effect for inhibiting growth of gram-positive bacteria.

Following the test procedure described below with agar substrates containing the compounds, we determined the concentration of the compounds necessary to inhibit the growth of various micro-organisms.

According to the test procedure, 1 ml of a solution of the compound of predetermined concentration is placed in a Petri dish and there is added 19 ml of molten common agar substrate, the mixture is agitated to make same uniform and then is cooled to harden the substrate. A platinum loop of bacteria liquor containing a million bacterial cells per milliliter is applied to the surface of the substrate and is cultured for 72 hours in a constant temperature room at 30° C. The minimum concentration of the compound in the substrate effective for inhibiting the growth is determined by examining the growth of the organism.

In the following tables, the indicia therein signify the following:

+: Microorganisms grow well. No effect of inhibiting the growth thereof is observed.

±: Microorganisms grow moderately. A moderate effect of inhibiting growth is observed.

—: Growth is stopped. The effect for inhibiting the growth is satisfactory.

The obtained results are shown in Table I.

Table 1

| | Minimum concentration for inhibiting the growth (p.p.m.) | | | | | |
|---|---|---|---|---|---|---|
| | Staphylococcus aureus | | | Bacillus subtilis | | |
| Compound | 1000 | 500 | 100 | 1000 | 500 | 100 |
| n-C$_4$H$_9$—S—CH=CHCON(CH$_2$CH$_2$OH)$_2$ | — | ± | + | — | + | + |
| n-C$_4$H$_9$—S(=O)—CH=CHCON(CH$_2$CH$_2$OH)$_2$ | — | — | — | — | — | ± |
| n-C$_4$H$_9$—S(=O)$_2$—CH=CHCON(CH$_2$CH$_2$OH)$_2$ | — | — | + | — | — | + |
| n-C$_7$H$_{15}$CON(CH$_2$CH$_2$OH)$_2$ (reference) | ± | + | + | — | + | + |

Table 1-continued

| Compound | Minimum concentration for inhibiting the growth (p.p.m.) | | | | | |
|---|---|---|---|---|---|---|
| | Staphylococcus aureus | | | Bacillus subtilis | | |
| | 1000 | 500 | 100 | 1000 | 500 | 100 |
| HO—⟨C6H4⟩—CO2C2H5 (reference) | − | − | + | − | ± | + |

EXAMPLE 2

The effective of the chain length of $R_1$ on inhibiting the growth of the organisms.

The results obtained by tests similar to those of Example 1 are shown in Table 2.

Table 2

| Compound | Minimum concentration for inhibiting the growth (p.p.m.) | | | | | | | | |
|---|---|---|---|---|---|---|---|---|---|
| | Staphylococcus aureus | | | Bacillus subtilis | | | Escherichia coli | | |
| | 1000 | 500 | 100 | 1000 | 500 | 100 | 1000 | 500 | 100 |
| n-C4H9—S(O2)—CH=CH—CON(CH2CH2OH)2 | − | − | − | − | − | − | − | ± | + |
| n-C6H13—S(O2)—CH=CHCON(CH2CH2OH)2 | − | − | − | − | − | ± | − | + | + |
| n-C8H17—S(O2)—CH=CHCON(CH2CH2OH)2 | − | − | − | − | − | + | − | + | + |
| n-C10H21—S(O2)—CH=CH—CON(CH2CH2OH)2 | − | − | − | − | + | + | ± | + | + |
| n-C12H25—S(O2)—CH=CHCON(CH2CH2OH)2 | − | − | − | − | − | − | − | + | + |
| n-C14H29—S(O2)—CH=CHCON(CH2CH2OH)2 | − | − | + | − | − | + | + | + | + |
| n-C16H32—S(O2)—CH=CHCON(CH2CH2OH)2 | − | + | + | − | + | + | + | + | + |
| n-C11H23CON(CH2CH2OH)2 (reference) | − | + | + | − | ± | + | + | + | + |
| ⟨C6H4⟩(COONa)(OH) (reference) | − | + | + | − | + | + | ± | + | + |
| HO—⟨C6H4⟩—CO2C2H5 (reference) | − | − | + | − | ± | + | − | ± | + |

| Compound | Proteus vulgaris | | | Pseudomonas aeruginosa | | |
|---|---|---|---|---|---|---|
| | 1000 | 500 | 100 | 1000 | 500 | 100 |
| n-C4H9—S(O2)—CH=CH—CON(CH2CH2OH)2 | − | − | + | − | + | + |
| n-C16H13—S(O2)—CH=CHCON(CH2CH2OH)2 | − | + | + | + | + | + |
| n-C8H17—S(O2)—CH=CHCON(CH2CH2OH)2 | ± | + | + | + | + | + |
| n-C10H21—S(O2)—CH=CH—CON(CH2CH2OH)2 | + | + | + | + | + | + |
| n-C12H25—S(O2)—CH=CHCON(CH2CH2OH)2 | − | + | + | ± | + | + |
| n-C14H29—S(O2)—CH=CHCON(CH2CH2OH)2 | + | + | + | + | + | + |
| n-C16H32—S(O2)—CH=CHCON(CH2CH2OH)2 | + | + | + | + | + | + |

Table 2-continued

| | Minimum concentration for inhibiting the growth (p.p.m.) | | | | | |
|---|---|---|---|---|---|---|
| n-C$_{11}$H$_{23}$CON(CH$_2$CH$_2$OH)$_2$ (reference) | + | + | + | + | + | + |
| ![salicylate] COONa / OH (reference) | ± | + | + | + | + | + |
| HO—C$_6$H$_4$—CO$_2$C$_2$H$_5$ (reference) | − | − | + | ± | + | + |

EXAMPLE 3

Effect of inhibiting the growth of microorganism.

The results obtained by tests similar to those of Example 1 are shown in Table 3.

Table 3

| | Minimum concentration for inhibiting the growth (p.p.m) | | | | | | | | |
|---|---|---|---|---|---|---|---|---|---|
| | Staphyloccus aureus | | | Bacillus subtilis | | | Escherichia coli | | |
| Compound | 1000 | 500 | 100 | 1000 | 500 | 100 | 1000 | 500 | 100 |
| n-C$_4$H$_9$—S—CH=CH—CONH$_2$ | − | − | + | − | ± | + | ± | + | + |
| n-C$_4$H$_9$—S(=O)—CH=CH—CONH$_2$ | − | − | − | − | − | − | − | ± | + |
| n-C$_4$H$_9$—S(O)(O)—CH=CH—CONH$_2$ | − | − | + | − | − | + | − | + | + |
| n-C$_4$H$_9$—S(=O)—CH=CH—CON(CH$_3$)$_2$ | − | − | − | − | − | − | − | + | + |
| n-C$_4$H$_9$—S(=O)—CH=CH—CON(CH$_2$CH$_2$OH)$_2$ | − | − | − | − | − | − | − | ± | + |
| n-C$_8$H$_{17}$—S(=O)—CH=CH—CON(CH$_2$CH$_2$OH)$_2$ | − | − | − | − | − | + | − | + | + |
| n-C$_4$H$_9$—S(=O)—CH=CH—CONHCH$_2$CH$_2$SO$_3$Na | − | − | + | − | − | + | + | + | + |
| n-C$_4$H$_9$—S(=O)—CH=CH—CONHCH$_2$CH$_2$COONa | − | − | − | − | − | + | ± | + | + |
| n-C$_{11}$H$_{23}$CON(CH$_2$CH$_2$OH)$_2$ (reference) | − | + | + | − | ± | + | + | + | + |
| COONa / OH (reference) | − | + | + | − | + | + | ± | + | + |
| HO—C$_6$H$_4$—CO$_2$C$_2$H$_5$ (reference) | − | − | + | − | ± | + | − | ± | + |

| | Proteus vulgaris | | | Pseudomonas aeruginosa | | |
|---|---|---|---|---|---|---|
| Compound | 1000 | 500 | 100 | 1000 | 500 | 100 |
| n-C$_4$H$_9$—S—CH=CH—CONH$_2$ | ± | + | + | + | + | + |
| n-C$_4$H$_9$—S(=O)—CH=CH—CONH$_2$ | − | ± | + | − | + | + |
| n-C$_4$H$_9$—S(O)(O)—CH=CH—CONH$_2$ | − | + | + | ± | + | + |

Table 3-continued

| Compound | Minimum concentration for inhibiting the growth (p.p.m) | | | | | |
|---|---|---|---|---|---|---|
| n-C$_4$H$_9$—S(=O)—CH=CH—CON(CH$_3$)$_2$ | − | − | ± | − | + | + |
| n-C$_4$H$_9$—S(=O)—CH=CH—CON(CH$_2$CH$_2$OH)$_2$ | − | − | + | − | + | + |
| n-C$_8$H$_{17}$—S(=O)—CH=CH—CON(CH$_2$CH$_2$OH)$_2$ | ± | + | + | + | + | + |
| n-C$_4$H$_9$—S(=O)—CH=CH—CONHCH$_2$CH$_2$SO$_3$Na | + | + | + | + | + | + |
| n-C$_4$H$_9$—S(=O)—CH=CH—CONHCH$_2$CH$_2$COONa | + | + | + | + | + | + |
| n-C$_{11}$H$_{23}$CON(CH$_2$CH$_2$OH)$_2$ (reference) | + | + | + | + | + | + |
| 2-hydroxybenzoic acid sodium salt (COONa, OH on benzene) (reference) | ± | + | + | + | + | + |
| HO—C$_6$H$_4$—CO$_2$C$_2$H$_5$ (reference) | − | − | + | ± | + | + |

EXAMPLE 4

| | |
|---|---|
| Sodium polyoxyethylene (3) lauryl-ether sulfate | 1.2% |
| Polyoxyethylene (15) lauryl-ether | 3% | was added lauric diethanolamide (reference) as a stabilizer or a formula (I) compound of the present invention. The detergent was tested for the properties of light-duty liquid detergent and the antiseptic effect. The obtained results are shown in Table 4.

Table 4

| Compound | Concentration (%) | Antiseptic effect Test period | | | Transparency | | Foaming power | Permeating power | Specific Surface tension |
|---|---|---|---|---|---|---|---|---|---|
| | | 1 day | 15 days | 30 days | −3° C. 2 days | amb. temp. 10 days | | | |
| n-C$_8$H$_{17}$—S—CH=CH—CON(CH$_2$CH$_2$OH)$_2$ | 3.5 | + | ± | − | transparent | transparent | 211cm | 8.6sec | 0.49 |
| n-C$_8$H$_{17}$—S(=O)—CH=CH—CON(CH$_2$CH$_2$OH)$_2$ | 3.5 | ± | − | − | transparent | transparent | 208cm | 8.5sec | 0.47 |
| n-C$_8$H$_{17}$—S(=O)$_2$—CH=CH—CON(CH$_2$CH$_2$OH)$_2$ | 3.5 | + | − | − | semi-transparent | transparent | 202cm | 8.2sec | 0.48 |
| n-C$_{11}$H$_{23}$CON(CH$_2$CH$_2$OH)$_2$ (reference) | 3.5 | + | + | + | transparent | transparent | 210cm | 8.5sec | 0.48 |
| n-C$_{11}$H$_{23}$CON(CH$_2$CH$_2$OH)$_2$ (reference) + benzoic acid sodium salt | 3.5 + 1.0 | + | + | + | transparent | transparent | 205cm | 8.7sec | 0.47 |
| n-C$_{11}$H$_{23}$CON(CH$_2$CH$_2$OH)$_2$ (reference) + 2-hydroxybenzoic acid sodium salt | 3.5 + 1.0 | + | + | + | transparent | transparent | 213cm | 8.6sec | 0.48 |

| | |
|---|---|
| Urea | 4% |
| EDTA | 0.4% |
| Water | q.s. |

A light-duty liquid detergent was prepared by mixing the above-listed components. To this detergent there

EXAMPLE 5

| | |
|---|---|
| Sodium dodecyl-benzenesulfonate | 8% |

| | |
|---|---|
| -continued | |
| Beef tallow-fatty acid sodium salt | 2% |
| Liquid paraffin | 90% |

To an emulsion-type cutting oil, prepared by emulsifying the above composition in 20 times its weight of tap water, there is added the compound of the present invention, or sodium salicylate (reference), or ethyl-p-hydroxybenzoate (reference). The mixture was agitated to emulsify it. These mixtures are inoculated with a mixed microbial emulsion containing a microbe concentration of $10^6$ cells/ml, of three strains of Pseudomonas aeruginosa IFO 3898, 3919, 3924 and one strain of Escherichia Coli IFO 3806. The compositions then are cultured with agitation at a constant temperature of 30° C. The numbers of microbes/ml of the sample after 30 days are determined by the mixing/dilution test method to evaluate the antiseptic effect. The obtained results are shown in Table 5.

EXAMPLE 6

An emulsion is prepared from 20% of liquid paraffin, 5% of polyoxyethylene (5) laurylether, 15% of the compound of the present invention, or sodium laurylsulphate, and the balance is water. Microorganisms obtained from the dust from the floor, wall and air inside a cosmetics plant and a detergent plant and from dirty water are cultured three days at 30° C. to prepare a microbial liquor for the experiment. One hundred ml of said emulsion composition are inoculated with 1 ml of said microbial liquor, and after 30 days' cultivation, a platinum loopful sample taken from the cultivation is inoculated in a bouillon substrate and cultured 72 hours at 30° C. The cultured liquor is evaluated with a turbidimeter to determine the antiseptic effect. On the other hand, the emulsification power of the composition is determined by placing the emulsion composition in a Ukena tube, shaking it for 30 mintues and then allowing it to stand still for 24 hours. The separated volume is Table 5

| Compound | Concentration (%) | Immediately after inoculation | Antiseptic effect Test period | | |
|---|---|---|---|---|---|
| | | | after 4 days | after 8 days | after 30 days |
| n-C$_4$H$_9$—S(=O)—CH=CH—CONH$_2$ | 0.5 | 78 × 10$^3$ | 8 × 10$^3$ | 0 × 10$^3$ | 0 × 10$^3$ |
| n-C$_4$H$_9$—S(=O)—CH=CH—CON(CH$_3$)$_2$ | 0.5 | 53 × 10$^3$ | 12 × 10$^3$ | 0 × 10$^3$ | 0 × 10$^3$ |
| n-C$_4$H$_9$—S(=O)—CH=CH—CON(CH$_2$CH$_2$OH)$_2$ | 0.5 | 69 × 10$^3$ | 3 × 10$^3$ | 0 × 10$^3$ | 0 × 10$^3$ |
| n-C$_4$H$_9$—S(=O)—CH=CH—CONHCH$_2$CH$_2$SO$_3$Na | 0.5 | 235 × 10$^3$ | 162 × 10$^3$ | 64 × 10$^3$ | 25 × 10$^3$ |
| n-C$_4$H$_9$—S(=O)—CH=CH—CONHCH$_2$CH$_2$COONa | 0.5 | 220 × 10$^3$ | 112 × 10$^3$ | 51 × 10$^3$ | 17 × 10$^3$ |
| 2-hydroxybenzoate (COONa, OH on benzene) (reference) | 1.0 | 938 × 10$^3$ | 807 × 10$^3$ | 651 × 10$^3$ | 712 × 10$^3$ |
| HO—C$_6$H$_4$—COOC$_2$H$_5$ (reference) | 1.0 | 851 × 10$^3$ | 722 × 10$^3$ | 504 × 10$^3$ | 628 × 10$^3$ | observed. The obtained results are shown in Table 6.

Table 6

| Compound | Antiseptic effect Test period | | | | Emulsion Condition |
|---|---|---|---|---|---|
| | Immediately after inoculation | After 4 days | After 8 days | After 30 days | |
| n-C$_8$H$_{17}$—S(=O)—CH=CH—CONHCH$_2$CH$_2$SO$_3$Na | + | — | — | — | Same emulsified condition as at the start |
| n-C$_8$H$_{17}$—S(=O)$_2$—CH=CH—CONHCH$_2$CH$_2$SO$_3$Na | + | — | — | — | Less stable emulsified condition than the starting emulsion |
| n-C$_8$H$_{17}$—S(=O)—CH=CH—CONHCH$_2$CH$_2$SO$_3$Na | + | — | — | — | Lower emulsification degree and far less stable condition than the starting composition |
| Sodium laurylsulfate | | | | | — |

EXAMPLE 7

A shampoo was prepared from the following ingredients:

| | |
|---|---|
| Polyoxyethylene laurylether | 15% |
| Sodium sulfate | 0.5% |
| Cetyl alcohol | 5.0% |
| Color and perfume | Small amounts |
| Water | q.s. |

To samples of the shampoo there were added various formula (I) compounds of lauric acid diethanolamide (reference compound). The antiseptic effect and the physicochemical properties of the compositions were examined. In these examinations, the antiseptic effect was evaluated similarly to Example 6, while the physicochemical properties of retention of viscosity, foaming behavior and foam stability, and long-term stability were measured. The determined values are expressed as percentages based on those obtained for the reference shampoo being taken as 100%.

The obtained results are shown in Table 7.

Table 7

| Compound | Concentration (%) | Antiseptic effect Test Period | | | Properties of Shampoo | | |
|---|---|---|---|---|---|---|---|
| | | After 7 days | After 15 days | After 30 days | Viscosity | Foam stability | Stability in long period |
| n-C$_4$H$_9$—S(=O)—CH=CH—CON(CH$_2$CH$_2$OH)$_2$ | 5.0 | — | — | — | 70 | 65 | 100 |
| n-C$_4$H$_9$—S(=O)—CH=CH—CON(CH$_2$CH$_2$OH)$_2$ | 5.0 | — | — | — | 65 | 60 | 100 |
| n-C$_4$H$_9$—S(=O)—CH=CH—CON(CH$_2$CH$_2$OH)$_2$ | 5.0 | — | — | — | 55 | 60 | 100 |
| n-C$_8$H$_{17}$—S(=O)—CH=CH—CON(CH$_2$CH$_2$OH)$_2$ | 5.0 | — | — | — | 100 | 100 | 100 |
| n-C$_8$H$_{17}$—S(=O)—CH=CH—CON(CH$_2$CH$_2$OH)$_2$ | 5.0 | — | — | — | 95 | 95 | 100 |
| n-C$_8$H$_{17}$—S(=O)—CH=CH—CON(CH$_2$CH$_2$OH)$_2$ | 5.0 | — | — | — | 90 | 90 | 100 |

The formula (I) compounds possess antimicrobial activity against one or more of bacteria, fungi and yeasts. They are useful in the same way as various known preservatives, such as lower alkyl esters of p-hydroxy benzoic acid, sodium salicylate and the like. They can be used to preserve various different perishable organic materials against attack and destruction by bacteria, fungi and yeast. Materials requiring such preservation are based on carbohydrates and proteins and various industrial and cosmetic compositions containing fats, oils, waxes and organic surfactants. The invention is based on the discovery of the antimicrobial activity of the formula I and their compatibility with other ingredients of cosmetic, detergent and cutting oil compositions. The other ingredients of the compositions can be any conventional ingredients used in the customary amounts.

The embodiments of the invention in which an exclusive property or privilege is claimed are defined as follows:

1. The method for minimizing deterioration of a non-pharmaceutical composition containing organic materials that are subject to attack and destruction by micro-organisms, which comprises adding to and blending in said composition a compound or a mixture of compounds having the formula

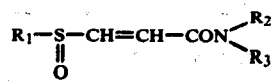

wherein $R_1$ is alkyl containing one to 8 carbon atoms or alkenyl containing up to 8 carbon atoms, and $R_2$ and $R_3$, which can be the same or different, are alkyl containing one to 20 carbon atoms in an amount effective to prevent or retard multiplication of micro-organisms in said composition.

2. The method according to claim 1 wherein said composition comprises one or a mixture of substances subject to deterioration by micro-organisms and selected from the group consisting of carbohydrates, proteins, fats, oils, waxes and organic surfactants.

3. The method according to claim 1 in which said composition is a liquid, cream or paste cosmetic composition.

4. The method according to claim 1 in which said composition is a liquid detergent composition.

5. The method according to claim 1 in which the amount of said compound is from 0.05 to 5 wt. %, based on the total weight of the composition.

6. The method according to claim 1 wherein

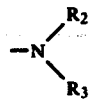

is dimethylamino.

7. The method according to claim 1 in which $R_1$ is alkyl having from 4 to 8 carbon atoms.

8. The method according to claim 7 in which

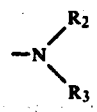

is dimethylamino.

9. The method according to claim 1 in which said compound has the formula

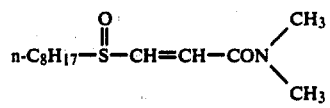

10. In a liquid, cream or paste cosmetic composition containing perishable organic materials subject to attack by micro-organisms, and containing a preservative effective to prevent growth of micro-organisms responsible for deterioration of the composition, the improvement which comprises; said preservative is a compound or a mixture of compounds having the formula

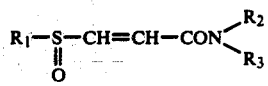

wherein $R_1$ is alkyl containing one to 8 carbon atoms or alkenyl containing up to 8 carbon atoms, and $R_2$ and $R_3$, which can be the same or different, are alkyl containing one to 20 carbon atoms and is present in an amount effective to prevent or retard multiplication of micro-organisms in said composition.

11. In an oil-in-water emulsion cutting oil composition containing perishable organic materials subject to attack by micro-organisms, and containing a preservative effective to prevent growth of micro-organisms responsible for deterioration of the composition, the improvement which comprises; said preservative is a compound or a mixture of compounds having the formula

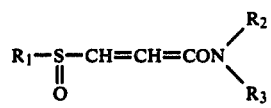

wherein $R_1$ is alkyl containing one to 8 carbon atoms or alkenyl containing up to 8 carbon atoms, and $R_2$ and $R_3$, which can be the same or different are alkyl containing one to 20 carbon atoms and is present in an amount effective to prevent or retard multiplication of micro-organisms in said composition.

12. In a liquid detergent composition consisting essentially of an aqueous solution of a synthetic organic surfactant subject to attack by micro-organisms, and containing a preservative effective to prevent growth of micro-organisms responsible for deterioration of the composition, the improvement which comprises; said preservative is a compound or a mixture of compounds having the formula

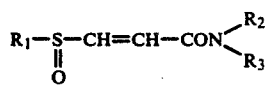

wherein $R_1$ is alkyl containing one to 20 carbon atoms or alkenyl containing up to 20 carbon atoms, and $R_2$ and $R_3$, which can be the same or different, are alkyl containing one to 20 carbon atoms, and is present in an amount effective to prevent or retard multiplication of micro-organisms in said composition.

* * * * *